United States Patent
Fallahpour

(10) Patent No.: US 11,931,521 B2
(45) Date of Patent: Mar. 19, 2024

(54) AUDIO-BASED OPERANT CONDITIONING FOR BRAIN TRAINING

(71) Applicant: Vital Neuro, Inc., New York, NY (US)

(72) Inventor: Kamran Fallahpour, New York, NY (US)

(73) Assignee: Vital Neuro, Inc., New York, NY (US)

( * ) Notice: Subject to any disclaimer, the term of this patent is extended or adjusted under 35 U.S.C. 154(b) by 0 days.

(21) Appl. No.: 18/133,180

(22) Filed: Apr. 11, 2023

(65) Prior Publication Data
US 2023/0321392 A1   Oct. 12, 2023

Related U.S. Application Data

(60) Provisional application No. 63/329,607, filed on Apr. 11, 2022.

(51) Int. Cl.
*A61M 21/02* (2006.01)
*A61B 5/375* (2021.01)
*A61B 5/38* (2021.01)

(52) U.S. Cl.
CPC ............. *A61M 21/02* (2013.01); *A61B 5/375* (2021.01); *A61B 5/38* (2021.01)

(58) Field of Classification Search
CPC .................. A61M 21/00–02; A61B 5/369–386
See application file for complete search history.

(56) References Cited

U.S. PATENT DOCUMENTS

| | | |
|---|---|---|
| 4,883,067 A | 11/1989 | Knispel et al. |
| 2015/0297108 A1* | 10/2015 | Chase ................ A61N 1/36025 434/236 |
| 2019/0269345 A1 | 9/2019 | Sriram |
| 2020/0368491 A1 | 11/2020 | Poltorak |
| 2021/0259557 A1* | 8/2021 | Frank ........................ G01J 3/50 |
| 2021/0353957 A1 | 11/2021 | Telfer et al. |

\* cited by examiner

*Primary Examiner* — Thaddeus B Cox
(74) *Attorney, Agent, or Firm* — Occhiuti & Rohlicek LLP

(57) ABSTRACT

Distributed feedback-circuitry uses operant conditioning to train a subject to achieve a target state of consciousness. The distributed feedback-circuitry includes remote circuitry having both a feature-extraction circuit and a controller. The former receives a real-time electroencephalogram and information indicative of a target state from the subject and generates a measured feature-set and a target feature-set therefrom. The latter causes transmission of a conditioning stimulus to be listened to by the subject. The conditioning stimulus causes the measured feature-set to be driven towards the target feature-set. The controller also causes the conditioning stimulus to comprise a conditioning-audio stimulus that transitions between being a base-audio stimulus with no reward stimulus and being a base-audio stimulus that has been operated on to incorporate a reward stimulus. The controller causes this transition based on progress made in causing the measured feature-set to conform to the target feature-set.

18 Claims, 3 Drawing Sheets

AUDIO-BASED OPERANT CONDITIONING FOR BRAIN TRAINING

CROSS REFERENCE TO RELATED APPLICATION

This application claims priority to U.S. Application No. 63/329,607, filed Apr. 11, 2022, the contents of which are hereby incorporated by reference in their it's entirety.

BACKGROUND

This invention relates to operant conditioning.

An electroencephalogram is typically dominated by frequencies within a particular band of frequencies. Both the dominance of a particular range of frequencies and the relationships between bands of frequencies have been found empirically to be associated with different states of consciousness. For example, an electroencephalogram dominated by very low frequencies, on the order 0.1 Hz to 3 Hz, is typically associated with sleep or a sense of detached awareness. Such an electroencephalogram is said to be dominated by "delta waves." One dominated by frequencies between about 5 Hz and 15 Hz has been found to be associated with a sense of relaxation, creativity, and visualization. This range if frequencies is often referred to as the "alpha waves."

It is generally desirable for a human to be able to switch between these various states of consciousness on demand. For instance, the ability to switch into a state dominated by delta waves on cue would be desirable for quickly falling asleep.

Unfortunately, many humans find it difficult to switch between brain states on demand. Those in the creative professions may find themselves waiting to reach a creative state and attempting all manner of peculiar ritual in an effort to arrive there sooner.

In some cases, this lack of control over one's state of consciousness is sufficiently extreme such that pharmaceuticals are used to artificially induce the desired state of consciousness.

SUMMARY

In one aspect, the invention features distributed feedback-circuitry that uses operant conditioning to train a subject to achieve a target state of consciousness. The distributed feedback-circuitry includes remote circuitry having both a feature-extraction circuit and a controller. The feature-extraction circuit receives a real-time electroencephalogram and information indicative of a target state from the subject. It then generates a measured feature-set and a target feature-set therefrom. Meanwhile, the controller causes transmission of a conditioning stimulus to be listened to by the subject. This conditioning stimulus causes the measured feature-set to be driven towards the target feature-set. The controller also causes the conditioning stimulus to comprise a conditioning-audio stimulus that transitions between being a base-audio stimulus with no reward stimulus and being a base-audio stimulus that has been operated on to incorporate a reward stimulus. The controller causes this transition based on progress made in causing the measured feature-set to conform to the target feature-set.

Embodiments include those in which the remote circuitry further includes a conditioner that generates the reward stimulus in response to a signal from the controller. In such embodiments, the controller causes the conditioning-audio stimulus to transition between being the base-audio stimulus and a combination of the base-audio stimulus and a tone that is in harmony with the base-audio stimulus.

In other embodiments, wherein the remote circuitry further includes a conditioner that generates the reward stimulus in response to a signal from the controller. In these embodiments, the base-audio stimulus is defined by a tonic frequency. This tonic frequency informs the controllers actions. In particular, the controller causes the conditioning-audio stimulus to transition between being the base-audio stimulus and a combination of the base-audio stimulus and tones having frequencies that are that are rational multiples of the tonic frequency.

Embodiments further include those in which the base-audio stimulus includes a musical composition that is missing a first feature. In such cases, the controller causes the conditioning-audio stimulus to transition between being the base-audio stimulus without the first feature and being a combination of the base-audio stimulus and the first feature. Examples of the feature include a particular track or a timbre.

Also among the embodiments are those in which the controller causes the conditioning-audio stimulus to transition between being the base-audio stimulus and being a combination of the base-audio stimulus and audio that causes perception of binaural beats or, in the alternative, a combination of the base-audio stimulus and an iso-chronic tone.

In still other embodiments, the base-audio stimulus has a first tempo and wherein the controller causes the conditioning-audio stimulus to transition between being the base-audio stimulus and the base-audio stimulus after having been modified to replace the first tempo with a second tempo.

In still other embodiments, the remote circuitry further includes a conditioner that includes a video generator that provides a video stimulus. In these embodiments, the conditioning stimulus includes the video stimulus.

Also among the embodiments are those in which the base-audio stimulus includes music that comprises a superposition of components. In such embodiments, the controller is configured to generate the conditioning-audio stimulus by modifying complex weights assigned to the components.

Still other embodiments include those in which the remote circuitry includes an audio-modification circuit that modifies frequency components of the base-audio stimulus so as to generate the conditioning-audio stimulus.

Embodiments also include those in which the controller causes the conditioning-audio stimulus to include the reward stimulus when the measured feature set and the target feature set have attained a pre-determined degree of similarity, those in which the controller causes the conditioning-audio stimulus to include the reward stimulus when the measured feature set is becoming increasingly similar to the target feature set, and those in which the controller causes the conditioning-audio stimulus to no longer include the reward stimulus when the measured feature set is moving away from the target feature set.

Among further embodiments are those in which the distributed feedback-circuitry includes a headset. The headset includes an electroencephalograph that is coupled to a wireless transmitter. These embodiments also include those that further comprise a smart phone that is in wireless communication with both the headset and with the feature extraction circuitry. In these embodiments, the smart phone executes an application that establishes communication with the feature extraction circuitry over a network.

Other embodiments include those in which the distributed feedback circuitry includes a plurality of local circuits, each of which is in communication with the remote circuit. In these embodiments, the conditioning stimulus is one of a plurality of conditioning stimuli, each of which is provided to a corresponding one of the local circuits.

Yet other embodiments are those in which the controller is configured to cause the transition by adding the reward stimulus to the base-audio stimulus and those in which it is configured to cause the transition by modifying the base-audio stimulus to incorporate the reward stimulus.

In another aspect, the invention features a method that includes receiving, from a subject, a real-time encephalogram from a subject and information indicative of a target state-of-consciousness, based on features in the encephalogram, forming a conditioning stimulus to cause a state-of-consciousness of the subject, as determined based on the real-time encephalogram, to move towards the target state-of-consciousness, and transmitting the conditioning stimulus to the subject. The formation of this conditioning stimulus includes providing a conditioning-audio stimulus that transitions between a first state and a second state. The first state provides positive reinforcement. The second state provides negative reinforcement.

In some embodiments, the remote circuitry includes application-specific circuitry that includes resistors, capacitors, inductors, transistors, and diodes together with a clock that controls the intervals in which charge is made to move through the various circuit elements. Among the circuit elements are arrays of semiconductor devices that maintain one of two desired states over time and that are made to transition between states at selected times.

The various steps carried out by the remote circuitry have proven to be incapable of being performed in a human mind given its current state of evolution. Indeed, it was for this reason that remote circuitry was required to implement the methods described herein.

Additionally, the various steps carried out by the remote circuitry have proven to be incapable of being performed have also been found to be incapable of being on a generic computer. Thus far, they have only been performed on a non-generic computer.

All attempts to cause the remote circuitry to perform the methods described herein in an abstract manner have thus far failed. Each attempt resulted in performance of the method in a non-abstract manner, where "non-abstract" is defined herein as the converse of "abstract" as that term is used by the Supreme Court of the United States.

The claims are explicitly defined to include only non-abstract implementations of the recited apparatus and methods, where "non-abstract" has been defined as above. Any party who presumes to construe the claims as being abstract in nature would simply be proving that it is possible to improperly construe the claims in a manner inconsistent with express statements to the contrary within the specification.

Other features and advantages of the invention are apparent from the following description, and from the claims.

DESCRIPTION

Figure 1:
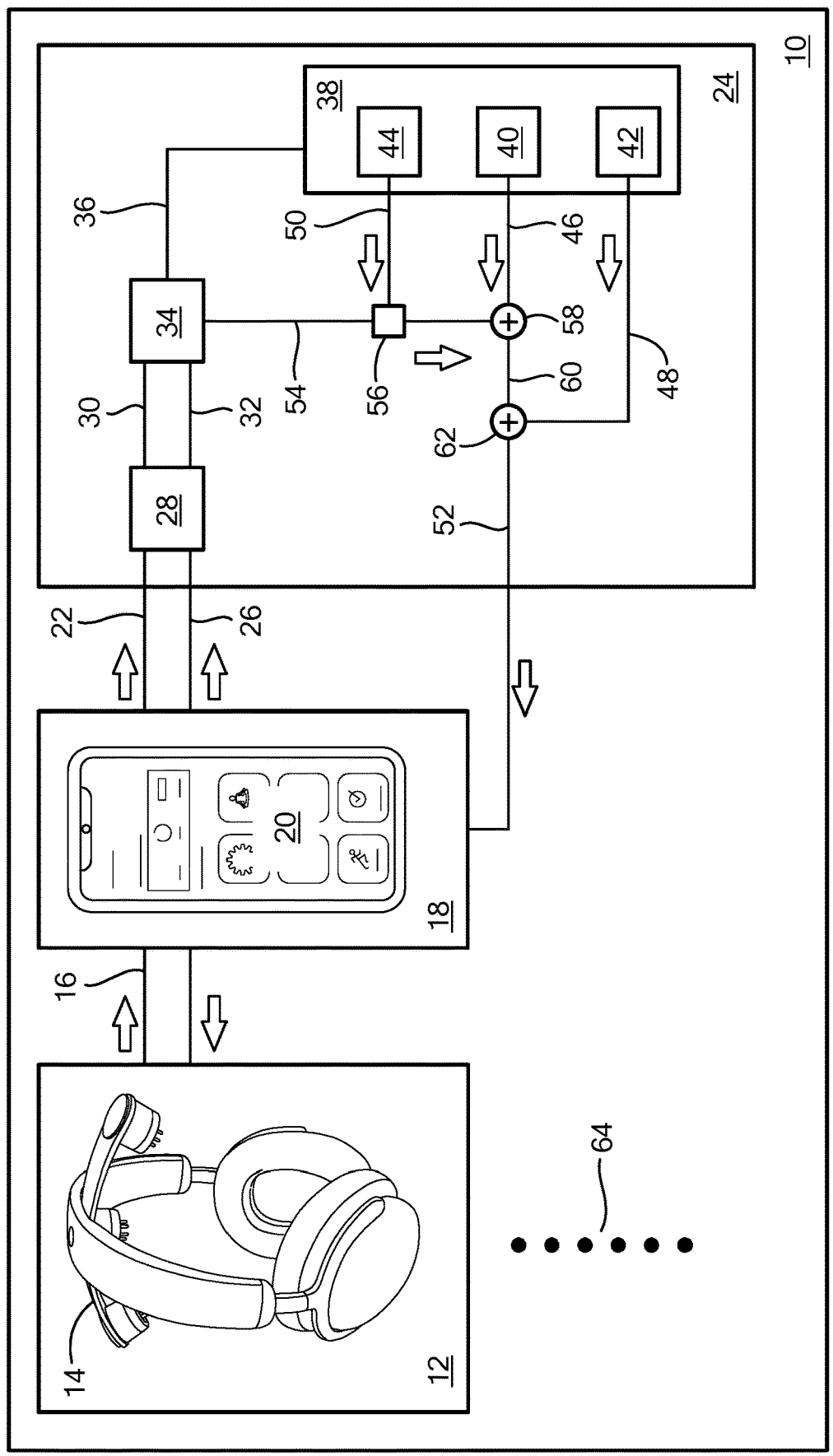
FIG. 1 shows distributed feedback-circuitry comprising a headset.

FIG. 1 shows distributed feedback-circuitry 10 for taking advantage of neuroplasticity to condition neurons in a subject's brain. The distributed feedback-circuitry 10 conditions the neurons into cooperating to cause a transition into a desired mental state and to thereafter cause the neurons to remain in that mental state. Examples of mental states include a relaxed state, a stress-reducing state, a state conducive to sleep, a state conducive to enhancement of focus, and a state conducive to greater attention. Other examples include a state of mindfulness, an energetic state, a happy state, and a state of flow.

The distributed feedback-circuitry 10 relies in part on inspection of features in real-time electroencephalogram measurements obtained from the subject. These measurements come by way of a headset 12 that comprises an electroencephalograph 14 that connects to a wireless transmitter that transmits a digitally-encoded real-time electroencephalogram 16 to local circuitry 18 that executes a training application 20. Examples of local circuitry 18 include portable devices, such as a smartphone, a tablet, smart jewelry, a smart watch, and a laptop. Other examples of local circuitry 18 include non-portable devices, such as a personal computer. This measurement signal includes a real-time electroencephalogram that is indicative of the subject's mental state.

In operation, the training application 20 will have received, from the subject, instructions indicative of a target mental state. The distributed feedback-circuitry 10 then attempts to urge the subject's mental state towards this target mental state based at least in part on the real-time encephalogram 16.

The training application 20 uses the real-time electroencephalogram 16 to display brain waves in real time on the local circuitry 18. In addition, the training application 20 causes the local circuitry 18 to forward a measurement signal 22 to remote circuitry 24 in the cloud. The measurement signal 22 incorporates the real-time electroencephalogram 16 therein. In addition, the training application 20 causes the local circuitry 18 to transmit target-state information 26 to the remote circuitry 24. This target-state information 26 comprises information indicative of what sort of neural conditioning the subject wishes to achieve.

The remote circuitry 24 includes a feature-extraction circuit 28 that carries out feature extraction on the measurement signal 22 to obtain a measured feature-set 30 for the subject. Based on the target-state information 26, the feature-extraction circuit 28 defines a target feature-set 32. It then provides both the target feature-set 32 and the measured feature-set 30 to a controller 34.

The controller 34 uses the target feature-set 32 and the measured feature-set 30 as a basis for providing a control signal 36 to a conditioner 38. The conditioner 38 comprises an audio generator 40, a video generator 42, and a reward generator 44. The audio generator 42 provides a base-audio stimulus 46; the video generator 42 provides a video stimulus 48; and the reward generator 44 provides a reward stimulus 50. The base-audio stimulus 46 and the occasional reward stimulus 50 combine to form a conditioning-audio stimulus 60. The conditional-audio stimulus 60 is then combined with the video stimulus 58 to form a conditioning stimulus 52. It is this conditioning stimulus 52 that is ultimately provided to the headset 12. This conditioning stimulus 52 provides positive or negative reinforcement to the subject in an attempt to condition the subject to reach the target feature-set 32.

The existence of positive or negative reinforcement in the conditioning stimulus 52 arises as a result of the controller 34 providing a reward signal 54 to control a reward switch 56. Depending on the state of the reward switch 56, a first adder 58 either combines the reward stimulus 50 with the base-audio stimulus 46 and removes the reward stimulus 50 from the base-audio stimulus 46. This controls whether the resulting conditioning-audio stimulus 60 provides positive reinforcement or negative reinforcement to the subject. A second adder 62 receives the conditioning-audio stimulus 60 and combines it with the video stimulus 48 to form the conditioning stimulus 52.

The reward signal 54 provided by the controller 34 thereby controls whether or not the conditioning stimulus 52 will comprise a superposition of the audio stimulus 60 and the reward stimulus 50 or just the audio stimulus 60 by itself. By controlling whether the reward stimulus 50 is present or absent based on the difference between the target feature-set 32 and the measured feature-set 30, the controller 34 carries out the conditioning in an effort to drive the measured-feature set 30 closer to the target feature-set 32.

The reward stimulus 50 is made to appear or disappear or is otherwise altered in response to the progress being made towards arriving at the target feature-set 32. In some embodiments, the reward stimulus 50 is a single tone whereas in others it is a weighted combination of frequencies having complex-valued weighting coefficients.

The subject's neurons are thus exposed to the conditioning stimulus 52 via the auditory pathway. This enables the conditioning process to be carried out. The controller 40 tailors the conditioning stimulus 52 to cause the measured feature-set 30 to transition into the target feature-set 32. It does so by reducing a difference between the measured feature-set 30, which is arriving at the controller 34 in essentially real time, and the target feature-set 32, which was provided by the training application 20 at the beginning of the conditioning process. This difference is reduced at least in part by the reward signal 54, which selectively adds or subtracts the reward stimulus 50 from the conditioning stimulus 52 as well as by the selection of content the reward stimulus 50 and the content of both the audio stimulus 60 and the video stimulus 48 so as to condition the subject's relevant neurons so that they achieve and maintain a desired brain state.

The remote circuitry 24 transmits the conditioning stimulus 52 to the training application 20. Upon receipt of the conditioning stimulus 52, the training application 20 separates the video stimulus 48 from the conditioning-audio stimulus 60 and displays the video stimulus 48 on the local circuitry 18. The training application 20 then sends the conditioning-audio stimulus 60 to the headset 12 to be listened to by the subject. As a result, the subject's neurons are exposed to the conditioning stimulus 52 using two different sensory pathways.

Like the conditioning-audio stimulus 60, the visual stimulus 48 reflects the real-time electroencephalogram measurements obtained from the subject. Accordingly, the details of the visual stimulus 48 change in response to changes in those electroencephalogram measurements. Preferably, the video stimulus 48 and the conditioning-audio stimulus 60 are synchronized. As a result, when the conditioning-audio stimulus 60 is changed, the video stimulus 48 sustains a corresponding change.

The training application 20 continues to receive measurement signals 60 from the electroencephalograph 14 as the subject is exposed to the conditioning stimulus 52. These are transmitted to the remote circuitry 24 to serve as a basis for feedback control over the neural conditioning process.

The remote circuitry 24 carries out further feature extraction on the measurement signal 22. The resulting updated measured feature-sets 30 provide a basis for evaluating the effect of the conditioning stimulus 52 and, in particular, the progress made towards driving the measured feature-set 30 towards the target feature-set 32. In response to the assessment of such progress, the controller 34 causes the conditioner 38 to formulates a revised conditioning-stimulus 52. It then transmits the revised conditioning-stimulus 52 back to the training application 20 so that the neurons to be conditioned can be exposed to them via the subject's sensory pathways.

The distributed feedback-circuitry 10 thus forms a distributed closed-loop feedback circuit that exposes the subject to a conditioning stimulus 52 in an effort to guide the subject's brain waves towards having the target feature set 32 through exposure to conditioning stimulus 52, with the conditioning stimulus 52 being adapted periodically in an effort to guide the received feature set towards the target feature set 32.

Moreover, the remote circuitry 24 is available for concurrent use by additional subjects 64 who interact with the remote circuitry 24 in the same manner using corresponding headsets 12 and local circuitry 18.

Figure 2:
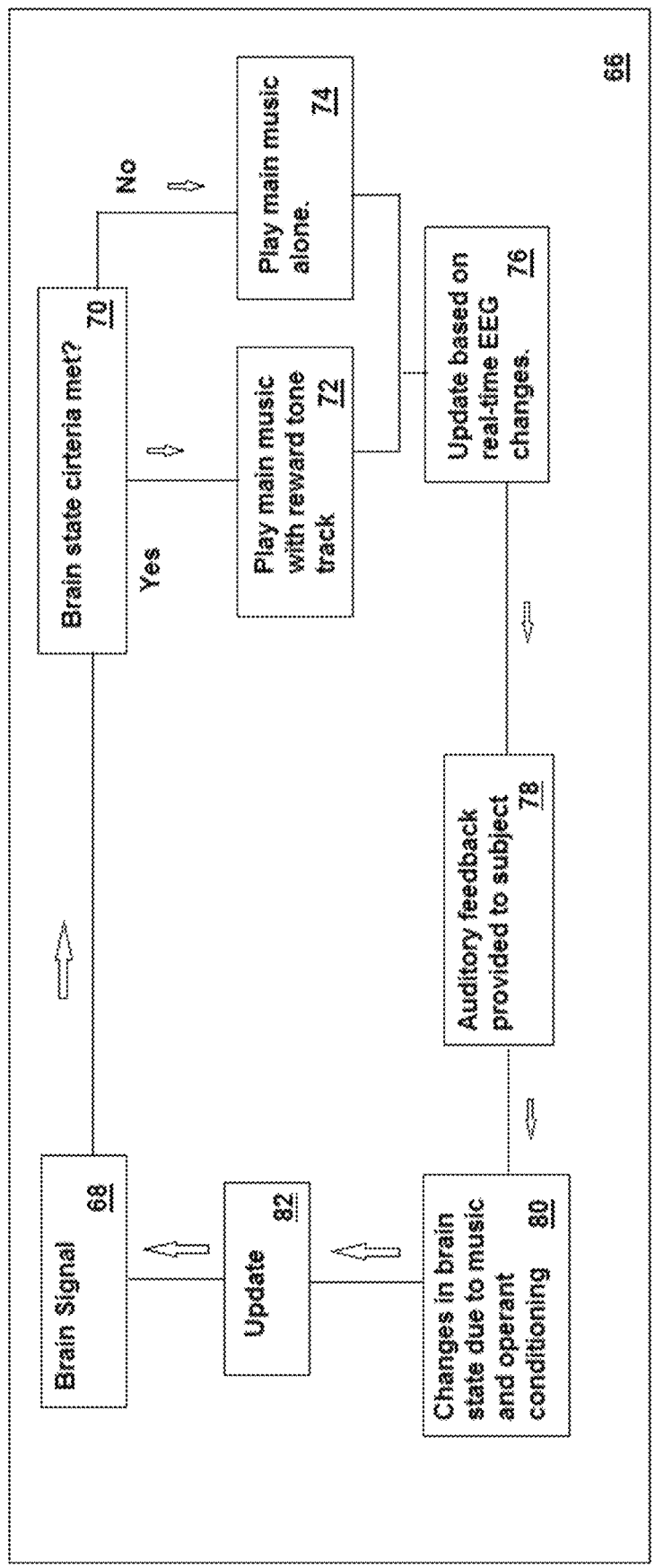
FIG. 2 is a method carried out by the distributed feedback-circuitry of FIG. 1.

FIG. 2 shows a method 66 carried out by the distributed feedback-circuitry 10 using real-time brain signals, which are captured by the headset 12, and predetermined brain state criteria, as embodied by the target feature-set 32, to guide real-time changes in music that is a constituent of the conditioning-audio stimulus 60 so as to guide the subject's brain into a desired state and to condition the subject's brain to learn how to maintain that state.

The method 66 begins with receipt of a measured feature-set 30 derived from the brain signal (step 68) and an inspection to see if that feature set conforms to a target feature-set 32 indicative of a desired brain state (step 70). If so, the reward signal 54 causes the reward switch 56 to add the reward stimulus 50 to the conditioning-audio stimulus 60 (step 72). Otherwise, the conditioning-audio stimulus 60 consists of only the base-audio stimulus 46 (step 74). In either case, the result is an updated conditioning-audio stimulus 60 that has been modified based on real-time changes to a received electroencephalogram from the subject (step 76). The resulting conditioning-audio stimulus 60 is then provided to the subject (step 78). As a result of exposure to the conditioning-audio stimulus 60, changes occur to the subject's brain state (step 80). These changes are manifested as an update to the measured feature-set 30 (step 82).

Figure 3:
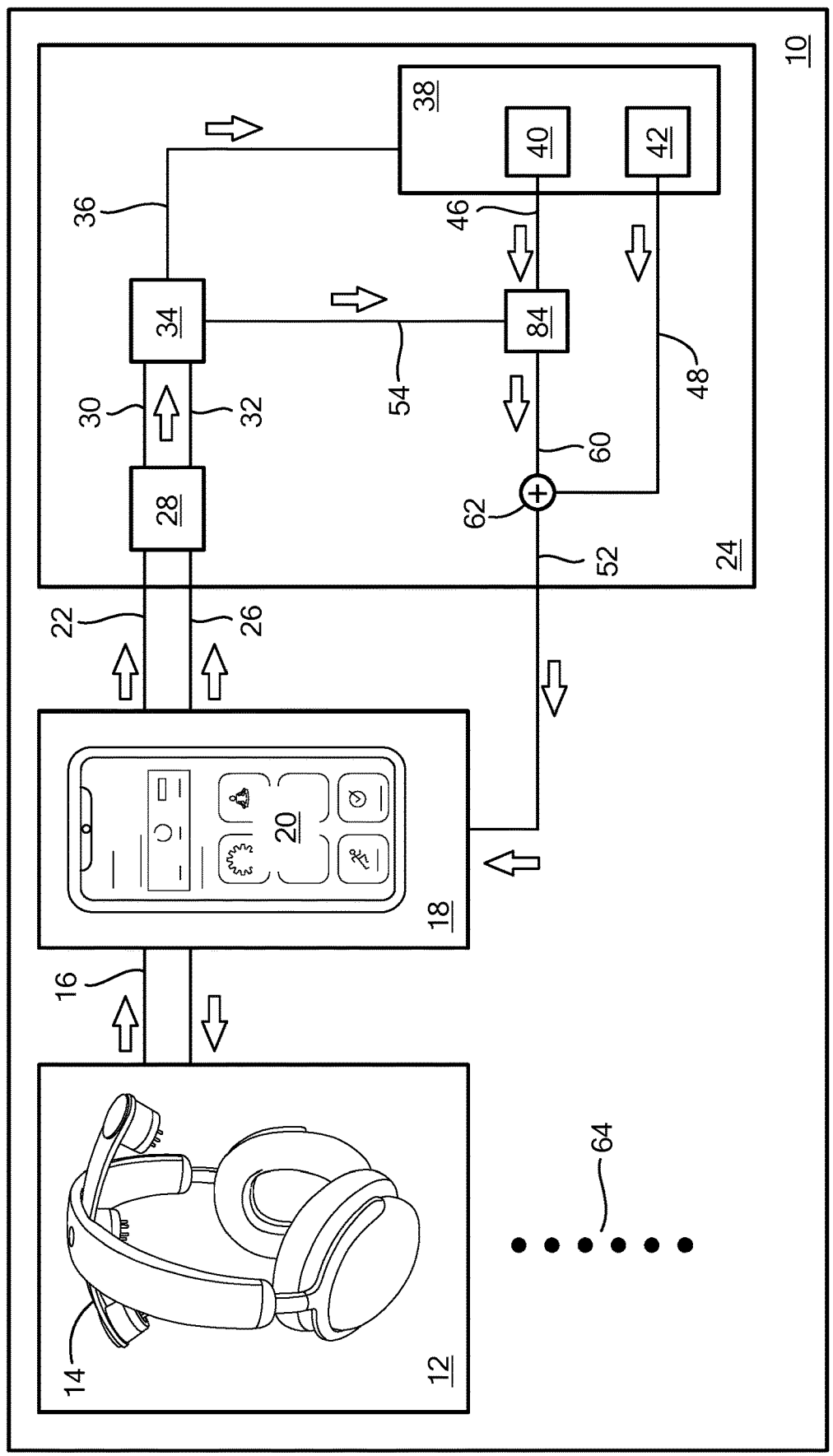
FIG. 3 is an alternative embodiment of the distributed feedback-circuitry of FIG. 1.

Referring now to FIG. 3, the base-audio stimulus 46 itself can be viewed as a superposition of frequency components weighted by, in general, complex values. The remote circuitry 24 would therefore be able to also vary the conditioning-audio stimulus 60 by modifying this superposition of the music's components. In such cases, the reward signal 54 triggers operation of an audio-modification circuit 84 that receives the base-audio stimulus 46 from the audio generator 40 and modifies it directly to form the conditioning-audio stimulus 60.

It should be apparent that FIG. 3 is a generalization of FIG. 1. The combination of the reward generator 44, the reward switch 56, and the first adder 58 as shown in FIG. 1 can readily be viewed as a particular implementation of the more general audio-modification circuit 84 in FIG. 3.

In some cases, the components of the base-audio stimulus 46 form an orthogonal basis of a function space. For example, the components can be complex exponentials. In such cases, the audio-modification circuit 84 adaptively varies the conditioning stimulus 52 to suppress or enhance certain frequencies of the base-audio stimulus 46 in an attempt to drive the brain waves to have the target feature-set 32.

In other cases, the components of the base-audio stimulus 46 do not form an orthogonal basis of the function space. For example, a first component could be the function that, when played by itself, contains the sounds made by the string section and a second component could be the function that, when played by itself, sounds the rest of the orchestra minus the string section from the first component. This granularity of components can be further increased. For example, the components may include a function that contains the sound played by a particular violin.

In either case, the audio-modification circuit 84 can individually weight the components whose superposition forms the base-audio stimulus 46, for example by a complex number, so as to modify the amplitude of that component and its phase relative to other components in an attempt to synthesize a conditioning-audio stimulus 60 to drive the features obtained from the measurement signal 22 towards the target feature-set 32. In effect, this generalizes the concept of the reward stimulus 50 from being a particular track that is simply added to the base-audio stimulus 46 to being an operator that operates on the base-audio stimulus 46 in a manner that is more complex than simply adding a track.

It should be noted that the act of modifying an existing musical composition by operating on it, for example by assigning weights to its components, effectively amounts to creating either a derivative work or a new composition, depending on the extent of the modification. As a result, the audio-modification circuit 84 can be viewed as adaptively composing a base-audio stimulus 46 or improvising off an existing base-audio stimulus 46 in an effort to condition neurons in the subject's brain to achieve a desired state, the desired state having been defined by the target features.

In still other embodiments, either the audio or video stimuli 46, 48 of the conditioning stimulus 52 is adaptively modified based on changes in brain state or in neural activity. Examples include causing the base-audio stimulus 46 to pause, changing the overall volume of the base-audio stimulus 46 as a whole or on a component-by-component basis, or changing the perceived source of the audio constituent, for example by varying the relative volumes heard on either loudspeaker of the headset 12.

In some embodiments, the audio-modification circuit 84 causes the conditioning-audio stimulus 60 to comprises adaptive music that responds in real time to real-time changes in the subject's physiology and, in particular, on activity within the subject's brain. In effect, the conditioning-audio stimulus 60 comprises music that has been composed or modified in such a way that various aspects of music will change in real time as in response to the subject's brain activity.

A variety of changes are contemplated as the conditioning-audio stimulus 60 adapts to different conditions. In some examples, pre-recorded tracks are added or removed from the conditioning-audio stimulus 60 in response to brain-related changes. In some cases, these tracks correspond to particular musical instruments or groups thereof. In other examples, the volume of the conditioning-audio stimulus 60 in response to brain-related changes in the subject.

Examples of the foregoing include embodiments in which the audio-modification circuit 84 changes the volume of a particular component of the base-audio stimulus 46 in response to brain-related changes in the subject. This would include the limiting case in which the audio-modification circuit 84 reduces the volume to zero, as a result of which the component disappears. Among these are embodiments in which the component whose volume is changed is a musical track.

The conditioning-audio stimulus 60 includes those components that are relied upon to achieve operant conditioning and those that are not. The latter serve primarily as a background upon which the former can be overlaid. Since these latter components are not relied upon for operant conditioning, they can be altered without compromising the function of operant conditioning.

In an effort to simultaneously achieve operant conditioning while avoiding repetition, certain embodiments include changing the latter components while preserving the former. This manifests as changing selected musical track volumes randomly or algorithmically. This ensures that the subject perceives novelty in the music while preserving those components of the conditioning-audio stimulus 60 that are responsible for operant conditioning.

In those embodiments that have two independent audio channels, one for each ear, the change to the conditioning-audio stimulus 60 takes the form of a change to the properties of the first and second channels independently of each other. For example, the volume in one channel may increase relative to that in the other channel in response to detection of brain-related changes in the subject. This can take place gradually to cause the illusion of movement in the source of the sound.

In some embodiments, such changes to the conditioning-audio stimulus 60 occur as a result of real-time changes in the subject's brain activity. These real-time changes include those indicative of having achieved a success threshold, those indicative of an achievement associated with passage of time or completion of an event, based on having achieved some criterion for a specified time, based on having achieved a sufficiently high level of some criterion for a sufficiently long time. Also contemplated are embodiments in which a variable schedule of reinforcement is used, in which case the changes to the conditioning-audio stimulus 60 will occur at random times according to some specified probability distribution.

Achievement of a success threshold is manifested by having achieved a predetermined threshold value based on combinations of features in the measured feature set 30, such as total amplitude within a band and other relationships between bands. Examples of such bands include the delta, theta, SMR, mid beta, high beta, and gamma bands.

Embodiments further include those in which the conditioning-audio stimulus 60 comprises music that has been composed and psycho-acoustically manipulated to help achieve particular predetermined target feature-sets 32 such as those associated with relaxation, meditation, and focus. Such manipulations include manipulations in tempo, rhythm, instrumentation, melodic patterns, harmonics, instrumentation, frequency emphasis, and orchestration that have been designed to promote a particular state-of-mind corresponding to a target feature-set 32.

Also among the embodiments are those in which the conditioning-audio stimulus 60 includes a pair of tones having almost the same frequency so as to cause perception of binaural beating, or a tone that is turned on and off at some regular rate, i.e., iso-chronic tones. Also among the embodiments are those in which the conditioning-audio stimulus 60 includes strategic spatial audio changes the enhancement of one or more particular frequencies, or the embedding of one or more particular frequencies.

A variety of sources are available for music associated with the base-audio stimulus 46. In some embodiments, the music has been specially composed for the occasion. In others, the music comes from a third-party music engine that has been pre-categorized by an artificial-intelligence engine and further processed to add appropriate conditioning elements as described above. In either case, the result is music that has been designed using neuroscientific and psycho-acoustic methods to promote achievement of particular mental states. Such music design includes manipulation of one or more musical and psycho-acoustic variable including tempo, rhythm, tones, including overall frequency balance and/or emphasis on lower or higher frequencies, such as bass and treble frequencies, timbre, musical texture, resonance, entrainment, which promotes a temporal locking of various physiological phenomena, such as motor activity, respiration, heart rate, and brain activity, with an external periodic signal, and overtones, which are used to reinforce perception of a fundamental frequency.

In some embodiments, the reward stimulus 50 comprises additional tracks that have been designed and composed strategically and specifically to be added to the main music track. Such a reward stimulus 50 is activated and heard in real-time as an additional layer of sound in addition to the base-audio stimulus 46 only when the subject has attained a pre-determined brain state. The subject's perception of this reward stimulus 50 provides feedback to the subject. This feedback indicates, to the subject, attainment of the target feature-set 32. In some embodiments, the reward stimulus 50 is a subtle one. An example of such a reward stimulus 50 is one that adds harmonics or overtones to the base-audio stimulus 46 so as to cause the subject to perceive a greater fullness to the sound. In other embodiments, the reward stimulus 50 also includes additional frequencies that have been strategically chosen to induce a particular brain state.

Because the distributed feedback-circuitry 10 has access to real-time electroencephalograms, it is able to learn the subject's response to particular stimuli. This allowed implementation of a machine-learning approach to enable the reward stimulus 50 to be fine-tuned to specific and personalized features of the subject's physiological signals, such as the subject's brain signature. As a result, it is possible to cause the reward stimulus 50 to adaptively change based on a subject's moment-to-moment success in moving towards the desired brain state.

In some embodiments, the alpha-peak frequency is calculated as a basis for automatically choosing one or more aspects of the reward stimulus 50. This process begins with monitoring certain features of a baseline electroencephalogram prior to a training session and calculating the alpha-peak frequency. Additional features of the reward stimulus 50 that match a particular base-audio stimulus 46 are generated or pre-composed with embedded frequencies to promote triggering of particular brain states. These embedded frequencies include overtones, resonant frequencies, and harmonics that harmonize with the musical key of the base-audio stimulus 46.

It is to be understood that the foregoing description is intended to illustrate and not to limit the scope of the invention, which is defined by the scope of the appended claims. Other embodiments are within the scope of the following claims.

What is claimed is:

1. An apparatus comprising distributed feedback-circuitry that uses operant conditioning to train a subject to achieve a target state of consciousness, said distributed feedback-circuitry comprising remote circuitry that comprises a feature-extraction circuit and a controller, wherein said feature-extraction circuit receives a real-time electroencephalogram and information indicative of a target state from said subject and generates a measured feature-set and a target feature-set therefrom, wherein said controller causes transmission of a conditioning stimulus to be listened to by said subject, said conditioning stimulus being one that causes said measured feature-set to be driven towards said target feature-set, wherein said controller causes said conditioning stimulus to comprise a conditioning-audio stimulus that transitions between being a base-audio stimulus with no reward stimulus and being a base-audio stimulus that has been operated on to incorporate a reward stimulus, wherein said controller causes said transition based on progress made in causing said measured feature-set to conform to said target feature-set, and wherein said base-audio stimulus comprises music comprising a superposition of components, and wherein said controller is configured to generate said conditioning-audio stimulus by modifying complex weights assigned to said components.

2. The apparatus of claim 1, wherein said base-audio stimulus comprises a musical composition that is missing a first track and wherein said controller causes said conditioning-audio stimulus to transition between being said base-audio stimulus without said first track and being a combination of said base-audio stimulus and said first track.

3. The apparatus of claim 1, wherein said controller causes said conditioning-audio stimulus to transition between being said base-audio stimulus and being a combination of said base-audio stimulus and audio that causes perception of binaural beats.

4. The apparatus of claim 1, wherein said base-audio stimulus has a first tempo and wherein said controller causes said conditioning-audio stimulus to transition between being said base-audio stimulus and said base-audio stimulus after having been modified to replace said first tempo with a second tempo.

5. The apparatus of claim 1, wherein said remote circuitry further comprises a conditioner that comprises a video generator that provides a video stimulus, wherein said conditioning stimulus comprises said video stimulus.

6. The apparatus of claim 1, wherein said remote circuitry comprises an audio-modification circuit that modifies frequency components of said base-audio stimulus so as to generate said conditioning-audio stimulus.

7. The apparatus of claim 1, wherein said controller causes said conditioning-audio stimulus to include said reward stimulus when said measured feature-set and said target feature-set have attained a pre-determined degree of similarity.

8. The apparatus of claim 1, wherein said controller causes said conditioning-audio stimulus to include said reward stimulus when said measured feature-set is becoming increasingly similar to said target feature-set.

9. The apparatus of claim 1, wherein said controller causes said conditioning-audio stimulus to no longer include said reward stimulus when said measured feature-set is moving away from said target feature-set.

10. The apparatus of claim 1, wherein said distributed feedback-circuitry comprises a headset comprising an electroencephalograph coupled to a wireless transmitter.

11. The apparatus of claim 1, wherein said distributed feedback-circuitry comprises a headset comprising an electroencephalograph coupled to a wireless transmitter and a smart phone that is in wireless communication with said headset and with said feature-extraction circuit, wherein said smart phone executes an application that establishes communication with said feature-extraction circuit over a network.

12. The apparatus of claim 1, wherein said distributed feedback-circuitry comprises a plurality of local circuits, each of which is in communication with said remote circuitry, wherein said conditioning stimulus is one of a plurality of conditioning stimuli, each of which is provided to a corresponding one of said local circuits.

13. The apparatus of claim 1, wherein said controller is configured to cause said transition by adding said reward stimulus to said base-audio stimulus.

14. The apparatus of claim 1, wherein said controller is configured to cause said transition by modifying said base-audio stimulus to incorporate said reward stimulus.

15. An apparatus comprising distributed feedback-circuitry that uses operant conditioning to train a subject to achieve a target state of consciousness, said distributed feedback-circuitry comprising remote circuitry that comprises a feature-extraction circuit and a controller, wherein said feature-extraction circuit receives a real-time electroencephalogram and information indicative of a target state from said subject and generates a measured feature-set and a target feature-set therefrom, wherein said controller causes transmission of a conditioning stimulus to be listened to by said subject, said conditioning stimulus being one that causes said measured feature-set to be driven towards said target feature-set, wherein said controller causes said conditioning stimulus to comprise a conditioning-audio stimulus that transitions between being a base-audio stimulus with no reward stimulus and being a base-audio stimulus that has been operated on to incorporate a reward stimulus, wherein said controller causes said transition based on progress made in causing said measured feature-set to conform to said target feature-set, and wherein said remote circuitry further comprises a conditioner that generates said reward stimulus in response to a signal from said controller, wherein said controller causes said conditioning-audio stimulus to transition between being said base-audio stimulus and a combination of said base-audio stimulus and a tone that is in harmony with said base-audio stimulus.

16. An apparatus comprising distributed feedback-circuitry that uses operant conditioning to train a subject to achieve a target state of consciousness, said distributed feedback-circuitry comprising remote circuitry that comprises a feature-extraction circuit and a controller, wherein said feature-extraction circuit receives a real-time electroencephalogram and information indicative of a target state from said subject and generates a measured feature-set and a target feature-set therefrom, wherein said controller causes transmission of a conditioning stimulus to be listened to by said subject, said conditioning stimulus being one that causes said measured feature-set to be driven towards said target feature-set, wherein said controller causes said conditioning stimulus to comprise a conditioning-audio stimulus that transitions between being a base-audio stimulus with no reward stimulus and being a base-audio stimulus that has been operated on to incorporate a reward stimulus, wherein said controller causes said transition based on progress made in causing said measured feature-set to conform to said target feature-set, and wherein said remote circuitry further comprises a conditioner that generates said reward stimulus in response to a signal from said controller, wherein said base-audio stimulus is defined by a tonic frequency, and wherein said controller causes said conditioning-audio stimulus to transition between being said base-audio stimulus and a combination of said base-audio stimulus and tones having frequencies that are that are rational multiples of said tonic frequency.

17. An apparatus comprising distributed feedback-circuitry that uses operant conditioning to train a subject to achieve a target state of consciousness, said distributed feedback-circuitry comprising remote circuitry that comprises a feature-extraction circuit and a controller, wherein said feature-extraction circuit receives a real-time electroencephalogram and information indicative of a target state from said subject and generates a measured feature-set and a target feature-set therefrom, wherein said controller causes transmission of a conditioning stimulus to be listened to by said subject, said conditioning stimulus being one that causes said measured feature-set to be driven towards said target feature-set, wherein said controller causes said conditioning stimulus to comprise a conditioning-audio stimulus that transitions between being a base-audio stimulus with no reward stimulus and being a base-audio stimulus that has been operated on to incorporate a reward stimulus, wherein said controller causes said transition based on progress made in causing said measured feature-set to conform to said target feature-set, and wherein said wherein said base-audio stimulus comprises a musical composition that is missing a first timbre and wherein said controller causes said conditioning-audio stimulus to transition between being said base-audio stimulus without said first timbre and being a combination of said base-audio stimulus and said first timbre.

18. An apparatus comprising distributed feedback-circuitry that uses operant conditioning to train a subject to achieve a target state of consciousness, said distributed feedback-circuitry comprising remote circuitry that comprises a feature-extraction circuit and a controller, wherein said feature-extraction circuit receives a real-time electroencephalogram and information indicative of a target state from said subject and generates a measured feature-set and a target feature-set therefrom, wherein said controller causes transmission of a conditioning stimulus to be listened to by said subject, said conditioning stimulus being one that causes said measured feature-set to be driven towards said target feature-set, wherein said controller causes said conditioning stimulus to comprise a conditioning-audio stimulus that transitions between being a base-audio stimulus with no reward stimulus and being a base-audio stimulus that has been operated on to incorporate a reward stimulus, wherein said controller causes said transition based on progress made in causing said measured feature-set to conform to said target feature-set, and wherein said controller causes said conditioning-audio stimulus to transition between being said base-audio stimulus and a combination of said base-audio stimulus and an iso-chronic tone.

* * * * *